United States Patent [19]

Zaiger et al.

[11] Patent Number: Plant 6,364

[45] Date of Patent: Nov. 1, 1988

[54] PEACH TREE ("PIX-ZEE")

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 947,089

[22] Filed: Dec. 29, 1986

[51] Int. Cl.[4] ..... A01H 5/03

[52] U.S. Cl. ..... Plt./43

[58] Field of Search ..... Plt./43

*Primary Examiner*—Robert E. Bagwill

[57] ABSTRACT

A new and distinct variety of peach tree which has the following unique combination of desirable features:

1. Dwarf tree size (5–7 feet at maturity).
2. Regular and heavy bearer.
3. Large size freestone fruit.
4. Fruit with good flavor and eating quality.
5. Fruit with attractive red skin color.
6. Attractive dense foliage.

1 Drawing Sheet

ORIGIN OF THE VARIETY

The new and distinct variety of dwarf peach tree was originated by us in the experimental orchard, located near Modesto, Calif., as a second generation seedling of a cross between a dwarf freestone nectarine of unknown parentage and Fayette Peach (Unpatented). A selection was made from the first generation seedlings and a large number of seed was collected from this selected seedling; these seeds were grown and maintained under careful and continual observation, during which time we recognized the desirable characteristics and selected the variety for asexual reproduction and commercialization.

ASEXUAL REPRODUCTION OF THE VARIETY

The present variety of peach tree was asexually reproduced by budding, as performed by us in our experimental orchard near Modesto, Calif. and shows that said characteristics come true to form and are established and transmitted through succeeding propagations.

SUMMARY OF THE VARIETY

The new and distinct variety of peach tree is of dwarf size, dense spreading growth, a regular and productive bearer of large size, firm, yellow flesh, freestone fruit. The fruit is further characterized by having good flavor and eating quality and having a high degree of attractive red skin color. The tree is further characterized by having a dwarf growth habit, close leaf nodes with heavy attractive foliage and large showy pink flowers.

BRIEF DESCRIPTION OF THE PHOTOGRAPHS

The accompanying photographs show reproductions of typical specimens of the fruit and foliage of the new variety of peach tree, with illustrations of the foliage, an exterior view of the fruit being shown and a fruit divided on its suture plane to reveal flesh coloration and showing a stone remaining in place. The photographs were taken shortly after being picked at maturity, (tree ripe) and the colors are as nearly true as is reasonably possible in a color representation of this type.

DESCRIPTION OF THE VARIETY

The botanical details of our new and distinct variety of peach tree and its flowers, foliage and fruit as based on observations of the specimens grown near Modesto, Calif., with color terminology in accordance with Reinhold Color Atlas by A. Korneruf and J. H. Wanscher.

Tree:
- *Size.*—Dwarf (5 to 7 feet at maturity).
- *Vigor.*—Non-vigorous.
- *Form.*—Spreading.
- *Density.*—Dense.
- *Production.*—Productive.
- *Bearing.*—Regular.

Trunk:
- *Size.*—Stocky.
- *Surface.*—Shaggy.
- *Color.*—Brown to brownish gray.

Branches:
- *Size.*—Stocky.
- *Texture.*—Shaggy.
- *Lenticels.*—Few. Large.
- *Color.*—Brown to brownish gray.

Leaves:
- *Size.*—Large. Average length — 7½" to 8". Average width — 1¼" to 1½".
- *Form.*—Lanceolate, pointed.
- *Texture.*—Smooth.
- *Thickness.*—Medium.
- *Margin.*—Crenate.
- *Petiole.*—Average length — 1". Average width — 3/32".
- *Glands.*—Average number 4, range 2 to 6. Positioned on lower portion of leaf blade and upper portion of petiole. Mixed — mostly Globose, few Reniform.
- *Color.*—Upper surface — deep green (27-F-5) to (28-F-6). Lower surface — grayish green (28-E-6) to (28-E-7).

Flower buds:
- *Size.*—Medium to large.
- *Form.*—Plump.
- *Pubescence.*—Pubescent.

Flowers:
- *Size.*—Large — showy.
- *Blooming period.*—Feb. 26, 1985 to Mar. 7, 1985. Varies slightly with climatic conditions.
- *Color.*—Pink.
- *Pollen.*—Present.

Fruit:

*Maturity when described.*—Tree ripe.
*Date of first picking.*—June 25, 1985.
*Date of last picking.*—July 5, 1985.
*Size.*—Large — comparitively uniform. Average diameter axially — $2\frac{1}{2}''$ to $3''$. Average diameter transversely to suture plane — $2\frac{1}{2}''$ to $3''$.
*Form.*—Globose — nearly symetrical.
*Suture.*—Shallow — extends from base to apex.
*Apex.*—Rounded to slight apex point.
*Base.*—Retuse.
*Cavity.*—Rounded to slightly elongated. Average depth — $\frac{1}{2}''$. Average breadth — $\frac{3}{4}''$.

Skin:
*Thickness.*—Medium.
*Texture.*—Medium.
*Tendency to crack.*—None.
*Down.*—Moderate — medium length.
*Color.*—Yellow ground color — (4-A-8) to (5-A-8) overspread with red — (8-A-7) to (8-B-8).

Flesh:
*Ripens.*—Fairly uniform. Slightly earlier near suture.
*Texture.*—Firm.
*Fibers.*—Few — tender.
*Juice.*—Moderate.
*Flavor.*—Mild.
*Eating quality.*—Good.
*Color.*—Yellow (4-A-7) to (4-A-8) to golden yellow (5-A-5) to (5-A-6).

Stone:
*Type.*—Freestone.

*Size.*—Medium. Average length — $1\frac{1}{8}''$. Average breadth — $\frac{7}{8}''$. Average thickness — $\frac{5}{8}''$.
*Form.*—Ovid.
*Base.*—Usually rounded — varies from straight to rounded.
*Apex.*—Cuspidate.
*Sides.*—Mostly equal.
*Surface.*—Furrowed toward apex, pitted toward base.
*Ridges.*—Rounded.
*Tendency to split.*—None.
*Color.*—Brown to brownish red (8-C-6) to (8-C-8).

Use: Dessert; local market.
Shipping quality: Fair to good.
Keeping quality: Good.

The new dwarf peach tree and its fruit herein described, may vary in slight detail due to climatic, soil conditions and cultural practices under which the variety may be grown, the present detailed description is that of the variety as grown by us in the experimental orchard under ecological conditions prevailing at Modesto, Calif.

The following is claimed:

1. A new and distinct variety of peach tree of dwarf size, dense spreading growth, and a regular and productive bearer of large size, firm, yellow flesh, freestone fruit, with good flavor, eating quality and attractive red skin color; the tree is further characterized by having a dwarf growth habit, close leaf nodes with heavy attractive foliage and large showy pink flowers.

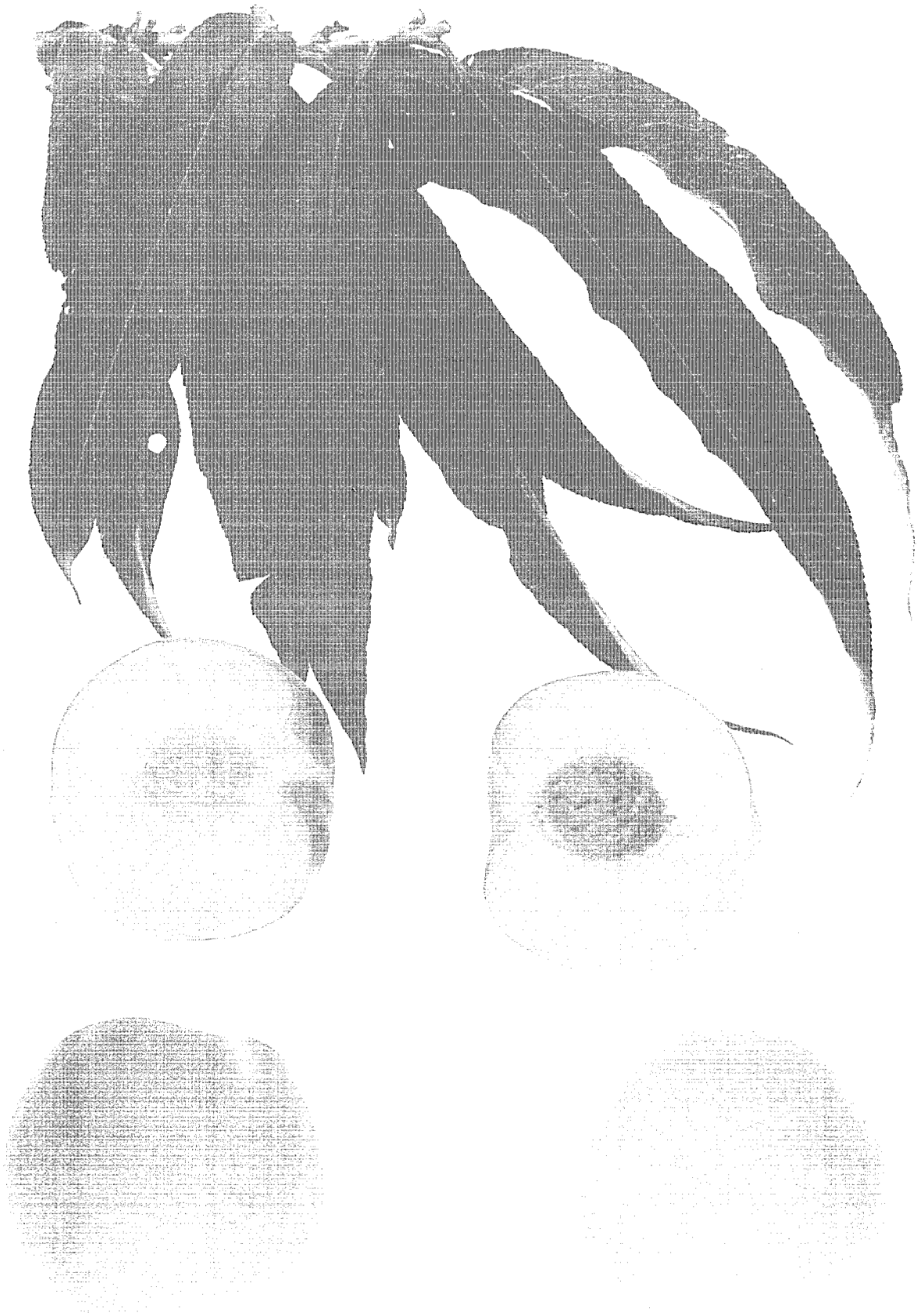

* * * * *